(12) United States Patent
Bessard et al.

(10) Patent No.: US 6,258,958 B1
(45) Date of Patent: Jul. 10, 2001

(54) PROCEDURE FOR PRODUCING FORMYL IMIDAZOLES

(75) Inventors: Yves Bessard, Sierre; Josef Heveling, Naters, both of (CH)

(73) Assignee: Lonza AG, Gampel/Wallis (CH)

( * ) Notice: Subject to any disclaimer, the term of this patent is extended or adjusted under 35 U.S.C. 154(b) by 0 days.

(21) Appl. No.: 09/719,380

(22) PCT Filed: Jun. 11, 1999

(86) PCT No.: PCT/EP99/04107

§ 371 Date: Dec. 11, 2000

§ 102(e) Date: Dec. 11, 2000

(87) PCT Pub. No.: WO99/65879

PCT Pub. Date: Dec. 23, 1999

(30) Foreign Application Priority Data

Jun. 15, 1998 (EP) .................................................. 98110868

(51) Int. Cl.$^7$ .................................................. C07D 233/22
(52) U.S. Cl. .......................................................... 548/333.5
(58) Field of Search ........................................... 548/333.5

(56) References Cited

U.S. PATENT DOCUMENTS

| 5,336,779 | * | 8/1994 | Yamamoto et al. | 548/333.5 |
| 6,040,475 | * | 3/2000 | Heveling et al. | 548/333.5 |
| 6,127,548 | * | 10/2000 | Mettler et al. | 548/333.5 |

FOREIGN PATENT DOCUMENTS

| 0 916 659 A1 | 5/1999 | (EP) . |
| 2 271 353 | 4/1994 | (GB) . |

* cited by examiner

Primary Examiner—Deborah C. Lambkin
Assistant Examiner—Golam M. M. Shameem
(74) Attorney, Agent, or Firm—Mary E. McCarthy; Stephen Venetianer; Charles M. Kinzig

(57) ABSTRACT

A new procedure for the catalytic conversion of hydroxy methyl imidazoles to formyl imidazoles is described. The catalysis takes place in the presence of a peroxide. Formyl imidazoles are important intermediate products for pharmaceutical substances.

7 Claims, No Drawings

PROCEDURE FOR PRODUCING FORMYL IMIDAZOLES

This application is a 371 of PCT/EP99/04107 Jun. 11, 1999.

SPECIFICATION

This invention concerns a new procedure for producing formyl imidazoles of the general formula

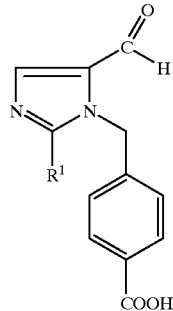

I in which $R^1$ means an alkyl group, by catalytic oxidation of hydroxy methyl imidazoles of the general formula

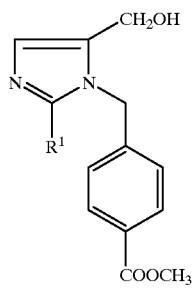

II in an alkaline milieu, in which $R^1$ has the meaning given above.

Formyl imidazoles are important intermediate products, for example, for the production of pharmaceutical substances such as diuretics or antihypertensives (WO-A 92/20651). Several procedures have previously been known for producing formyl imidazoles. In CH-A 685496, a procedure is described in which the catalytic oxidation of hydroxy methyl imidazoles to formyl imidazoles is performed in the presence of noble metal catalysts such as platinum/bismuth, platinum black, platinum or palladium on activated charcoal, with oxygen insufflation.

The task of the invention was therefore to make available an economical, improved procedure for producing formyl imidazoles.

In this invention, this task is solved by the procedure defined in claim 1. In claim 1, hydroxy methyl imidazoles of the general formula

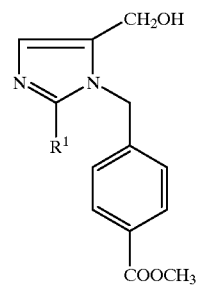

II in which $R^1$ has the meaning given above, are catalytically oxidized in an alkaline milieu in the presence of a noble metal catalyst and a peroxide to formyl imidazoles of the general formula

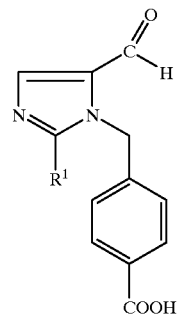

I in which $R^1$ has the meaning given above.

$R^1$ has the meaning of hydrogen or an alkyl group, and more particularly a straight-chained or ramified alkyl group with 1 to 6 C atoms. Specifically, this may be methyl, ethyl, propyl, isopropyl, butyl, isobutyl, tert, butyl, pentyl and its isomers as well as hexyl and its isomers. The preferred meaning of $R^1$ is butyl.

Hydroxy methyl imidazoles can be readily produced as starting compounds as specified, for example, in WO-A 92/20651 or as in E. F. Godefroi et al., Trav. Chim. Recueil Pays Bas, 91, 1383 (1972).

Platinum, palladium, rhodium or gold may be used as the noble metal catalyst. The noble metal is best used in combination with metals such as, for example, bismuth, lead, cerium or indium as the second component. The preferred catalysts are platinum/bismuth or platinum/lead.

The noble metal catalyst is used by itself or bound to a vehicle such as, for example, activated charcoal, silicon dioxide, aluminum oxide, silicon-aluminum oxide, zirconium oxide or titanium oxide. It is preferably bound to activated charcoal.

Noble metal catalysts bound to activated charcoal can be commercially obtained, for example, from Degussa.

The appropriate percentage of the noble metal bound to a vehicle is between 0.1 and 15% by weight, and preferably between 0.5 and 7% by weight, relative to the vehicle material.

The noble metal catalyst is preferably used in an amount of 0.05 to 1.0 mol % noble metal base relative to the hydroxy methyl imidazole, and an amount of 0.1 to 0.4 mol % noble metal base relative to hydroxy methyl imidazole is especially preferred.

Organic or inorganic peroxides are used as peroxides. Hydrogen peroxide, perborates, a percarboxylic acid, tert, butyl hydroperoxide, cumol hydroperoxide, perbenzoic acid, m-chloroperbenzoic acid, monoperphthalic acid or peracetic acid are well suited, for example. Hydrogen peroxide used in a 10% to 30% aqueous solution is particularly suitable.

In addition to the catalytic oxidation, the hydrolysis of the methyl ester of the hydroxymethyl imidazoles of general formula II takes place in an alkaline milieu.

The alkaline milieu is best obtained by the addition of an alkali hydroxide, an alkali carbonate or an alkali acetate to the reaction mixture. Alkali hydroxide is used preferably in a 1:0.05 to 5 ratio, and best in a 1:3 ratio, relative to the mol amount used of the hydroxymethyl imidazole of general formula II.

The catalytic oxidation takes place best in an alkaline milieu in the presence of water, a water-miscible solvent or mixtures thereof.

Particularly suitable water-miscibie solvents are, for example, alcohols or carboxylic acids with 1 to 6 C atoms or ketones such as, for example, acetone or methyl ethyl ketone.

Mixtures of water and water-miscible solvents are preferably used.

The catalytic oxidation is best performed at a temperature of 20° to 120° C., preferably at 50° to 100° C.

After the standard peroxide dosing time of 0.5 to 3 hours, the compound of general formula I can be isolated in the standard manner after a sufficient secondary reaction time.

The product is isolated by appropriate crystallization and filtration. The catalyst used can be used several times with no loss of activity.

EXAMPLES

Example 1

Production of 4-[(2-butyl-5-formyl-1H-imidazo-1-yl)methyl]benzoic acid 900 mg (3 mmol) of 4-[(2-butyl-5-hydroxymethyl-1H-imidazo-1-yl)methyl]benzoic acid methyl ester, 8 ml caustic soda solution (1M), 0.5 ml methanol and 107 mg platinum 5% and 5% bismuth on activated charcoal containing 60% water are placed in a 25-ml flask at room temperature and heated to 60° C.

0.8 g (4.6 mmol) 20% aqueous $H_2O_2$ solution was added to this suspension at 60° C. over 30 minutes and the mixture was then reacted with HPLC. Another 0.2 g (1.1 mmol) 20% aqueous $H_2O_2$ solution was then added over 10 minutes. Then 0.2 g (5 mmol) 20% NaOH was added. The reaction solution was heated for 2 hours at 100° C. The mixture was cooled to room temperature. The catalyst was filtered over celite and washed with 5 ml water. After acidification to pH 5.0 with HCl (15%), the product precipitated out. It was cooled to 2° C., filtered, washed with 2×5 ml water and dried at room temperature at 15 mbar. 410 mg (48%) yellow 4-[(2-butyl-5-formyl-1H-imidazo-1-yl)methyl]benzoic acid were obtained (HPLC content 96%).

Melting point: 144–146° C.

$^1$H-NMR (DMSO-$_{d6}$, 400 Mhz) δ:

12.9 (1H, s);
9.65 (1H, s);
7.94 (1H, s);
7.90 (2H, d);
7.11 (2H, d);
5.65 (2H, s);
2.63 (2H, t);
1.54 (2H, pent);
1.36 (2H, hex);
0.79 (3H, t).

What is claimed is:

1. Procedure for producing formyl imidazoles of the general formula

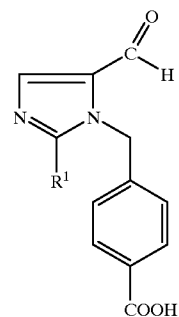

in which $R^1$ means an alkyl group, by catalytic oxidation of hydroxy methyl imidazoles of the general formula

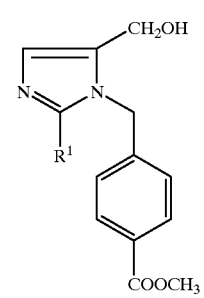

in which $R^1$ has the meaning given above, in the presence of a noble metal catalyst, characterized in that the catalytic oxidation takes place in the presence of a peroxide in an alkaline milieu.

2. Procedure as in claim 1, characterized in that $R^1$ is a butyl group.

3. Procedure as in claim 1, characterized in that the noble metal catalyst is a platinum/bismuth catalyst or a platinum/lead catalyst.

4. Procedure as in claim 1, characterized in that the peroxide is hydrogen peroxide.

5. Procedure as in claim 1, characterized in that the alkaline milieu is obtained by adding an alkali hydroxide, an alkali carbonate or an alkali acetate to the reaction mixture.

6. Procedure as in claim 1, characterized in that the catalytic oxidation is performed in the presence of water, a water-miscible solvent, or mixtures thereof, in an alkaline milieu.

7. Procedure as in claim 1, characterized in that the reaction is performed at a temperature of 20° to 120° C.

* * * * *